US005792071A

United States Patent [19]

Hein

[11] Patent Number: 5,792,071
[45] Date of Patent: Aug. 11, 1998

[54] SYSTEM FOR MULTI-SITE SKIN TESTING AND COMPONENTS THEREOF

[75] Inventor: Gary L. Hein, Oakley, Ill.

[73] Assignee: Lincoln Diagnostics, Decatur, Ill.

[21] Appl. No.: 583,771

[22] Filed: Jan. 11, 1996

[51] Int. Cl.$^6$ ................................................ A61B 5/00
[52] U.S. Cl. ........................................................ 600/556
[58] Field of Search ................................ 128/743, 744

[56] References Cited

U.S. PATENT DOCUMENTS

| | | |
|---|---|---|
| 2,522,305 | 9/1950 | Simon ........................... 128/743 |
| 3,136,314 | 6/1964 | Kravitz . |
| 3,556,080 | 1/1971 | Hein . |
| 4,711,247 | 12/1987 | Fishman ......................... 128/743 |
| 5,396,989 | 3/1995 | Hein . |

Primary Examiner—Max Hindenburg
Assistant Examiner—Pamela L. Wingood
Attorney, Agent, or Firm—Lockwood, Alex, FitzGibbon & Cummings

[57] ABSTRACT

A system for making multi-site skin tests primarily for use by allergists making use of a multi-head applicator and a matching multi-well dipwell tray. The applicator has an elongated handle with arms extending transversely from opposite sides having downwardly extending legs terminating in multi-pointed ends or heads capable of picking up and retaining small quantities of liquid skin-testing substances. The multi-point ends or heads occupy the same plane and are arrayed in a pattern suited for simultaneously making multi-site skin tests. The applicator cooperates with a multi-well dipwell tray with a plurality of dipwells arrayed in patterns which match the pattern in which the multi-pointed ends or heads on the cooperating applicator are arrayed. The individual dipwells have a capacity to hold quantities of skin testing substances or medicaments equaling many times the volume of a single dose or increment that is picked up by one of the multi-pointed ends or heads on an applicator. Both the applicator and dipwell tray have guidance formations thereon whereby the user can readily orient the multi-point pick-up ends or heads on the applicator with the dipwells so that the heads can be readily and accurately lowered into the matching dipwells without damaging the points of the applicator.

26 Claims, 2 Drawing Sheets

FIG.1
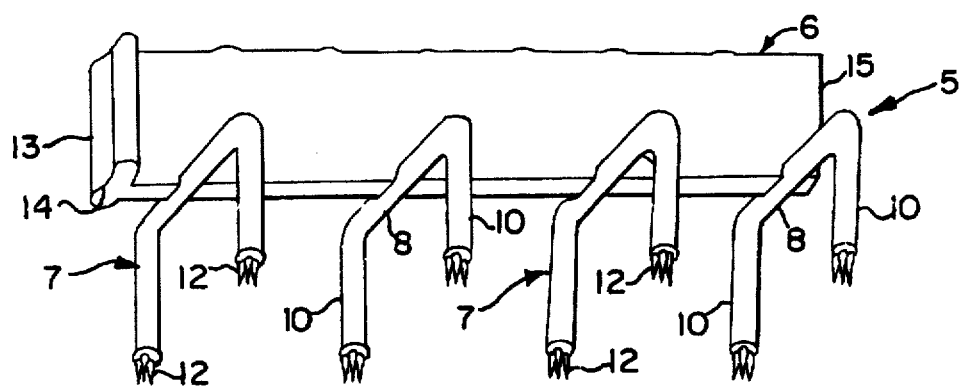
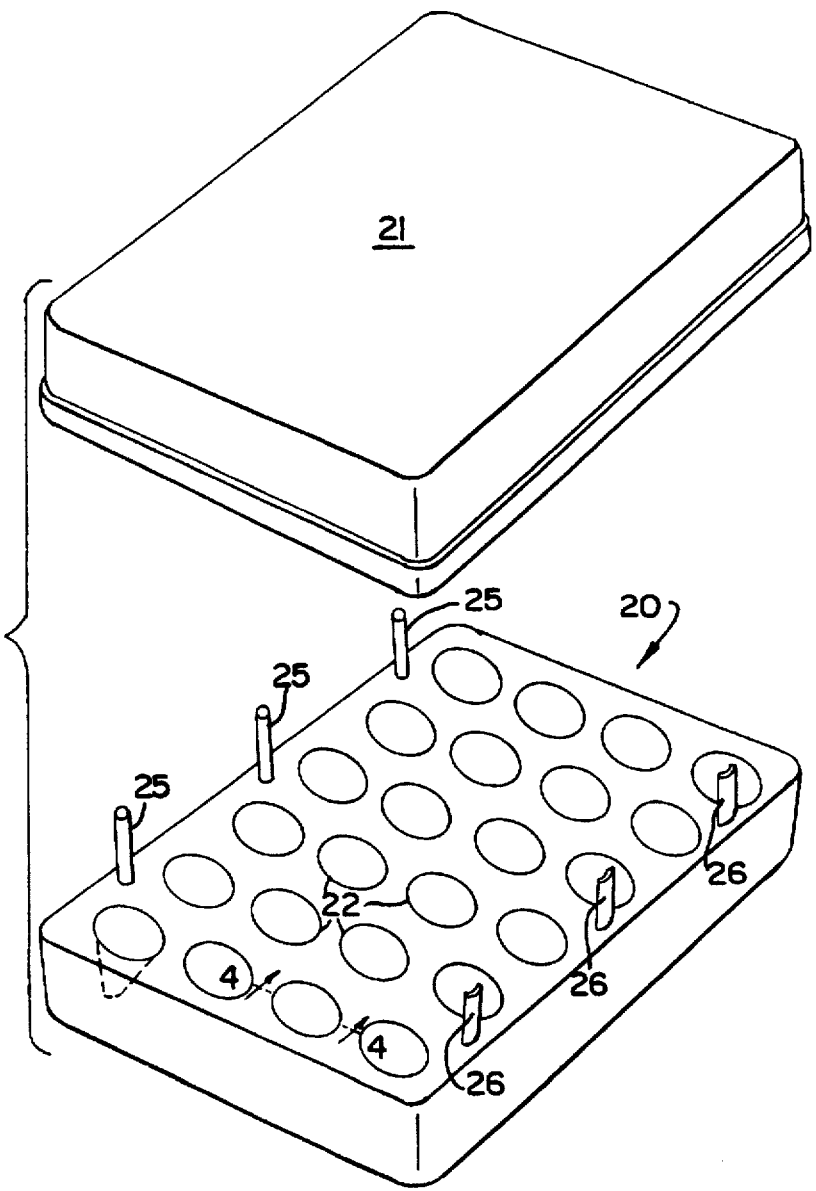
FIG.2

SYSTEM FOR MULTI-SITE SKIN TESTING AND COMPONENTS THEREOF

BACKGROUND OF THE INVENTION

This invention relates generally to an improved system for making multi-site skin tests and to new and improved components used in the system.

Applicant's U.S. Pat. No. 3,556,080 dated Jan. 19, 1971 discloses a system for making multi-site skin tests and components for use in the system. One of the components of the system disclosed in U.S. Pat. No. 3,556,080 is an applicator having a plurality of multi-point, skin-puncturing heads. A second component disclosed in the patent is a form of dipwell tray for use in conjunction with the applicator. The patent teaches loading the tray with different desired skin testing substances or medicaments such as skin test antigens and allergenic extracts and dipping the applicator heads into the dipwells whereby the multi-point, skin-puncturing heads pick up a load of skin testing substances. According to the patent, the operator then applies the loaded applicator to the skin of a person being tested so that the skin testing substance on each head is introduced at a spaced site on the person's skin. The diameter of each dipwell was of a size to admit the columnar or circular, point base of each head but not large enough to admit the entire head with its annular flange, limiting the points to picking up only two to three loads, which required frequent refilling to maintain an adequate fluid level.

While the complete system disclosed in U.S. Pat. No. 3,556,080 was not adopted in practice, the applicator itself, in a commercial form, was adopted and has gone into extensive use by the medical profession. However, the procedure for loading the individual multi-point, skin-puncturing heads has been entirely different from the procedure and method disclosed in the patent since the dipwell tray therein disclosed was not acceptable to the profession because only a few loads could be obtained from each well, requiring continuous refilling of the wells. Then too, it was difficult to place the applicator heads into each well without damaging the points. In the adopted and current procedure the applicator of U.S. Pat. No. 3,556,080 is inverted and the heads are manually loaded, one-by-one, a time-consuming procedure.

According to the present invention, improvements have been made in both the applicator and the dipwell tray of U.S. Pat. No. 3,556,080 whereby the problems and disadvantages associated with the system disclosed in the patent and the components thereof have been eliminated.

Accordingly, the object of the present invention, generally stated, is the providing of an improved system for multi-site skin testing based on the combined use of a novel applicator having multiple skin-puncturing points and a novel dipwell tray for containing an ample supply of skin testing substances to be picked up in small increments when using a series of disposable applicators.

Certain other objects and advantages of the invention will become apparent from the following description of preferred embodiments of the invention taken in connection with the accompanying drawings.

BRIEF DESCRIPTION OF THE DRAWINGS

FIG. 1 is a perspective view of an applicator for simultaneously picking up multiple doses or loads of skin testing substances and thereafter simultaneously making multiple skin tests on spaced sites on a person's skin in accordance with the present invention;

FIG. 2 is a perspective view of a dipwell tray serving as a reservoir for skin test substances to be withdrawn in relatively small increments by the applicator of FIG. 1 and thereafter applied to the skin by the applicator;

Referring to FIG. 1, an applicator is indicated generally at 5 therein comprising an elongated handle 6 from which a plurality of inverted U-shaped limbs 7—7 depend. Each limb 7 comprises a horizontal bight section 8 attached approximately at its mid-point to the underside of the handle 6 and a pair of downwardly extending legs 10—10. The distal ends of all legs 10 lie in approximately the same plane and each end has depending therefrom a multiplicity of skin puncturing points indicated generally at 12—12. For example, the multiplicity of points 12 may take the form of nine pressure-type sharp points clustered closely together so as to create a capillary effect between the points for holding liquid in the interstices or spaces between the points as disclosed in Kravitz U.S. Pat. No. 3,136,314. The disclosure of U.S. Pat. No. 3,136,314 is incorporated by reference herein. The cross sectional size of the legs 10 does not appreciably exceed the cross sectional size of the points 12.

Figure 3:
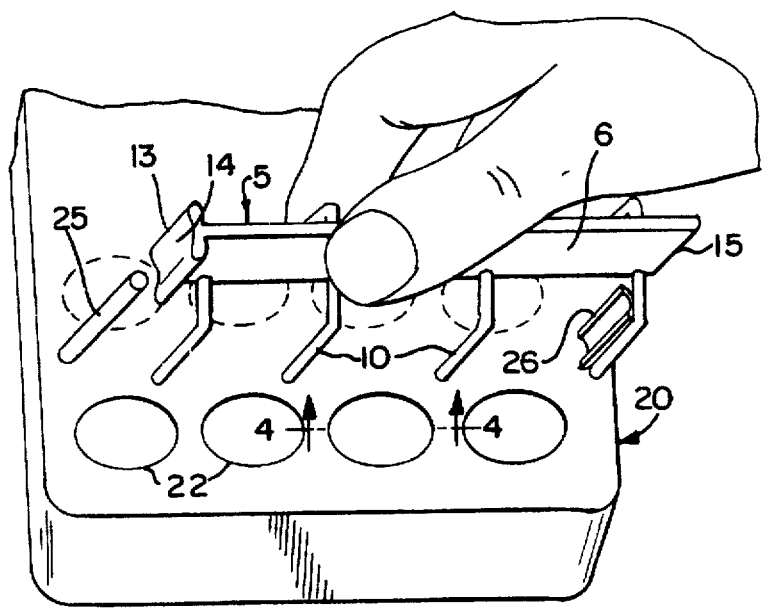
FIG. 3 is a fragmentary perspective view illustrating how the applicator of FIG. 1 is used in cooperation with the dipwell tray of FIG. 2.

The handle 6 is provided on one end with a guide formation indicated at 13 which extends generally transversely to the handle 6 with a vertically extending concave groove or recess 14 therein. Preferably, the applicator 5 will be integrally molded, such as by injection molding, from a suitable plastic. However, it could be formed from other materials by other methods. By injection molding the applicator 5 from a plastic the cost of these units can be reduced to the point where the applicators are disposable after a single use. Therefore, the applicators 5 can be sterilized prior to packaging and shipment so that the packages can be opened and the adapters used directly in a sterilized condition.

In FIG. 2, a dipwell tray is indicated generally at 20 which is designed for use with the applicator 5 of FIG. 1. Desirably, the dipwell tray 20 is provided with a cover 21 for protecting the contents of the dipwells when the tray is not in use. The tray 20 may be injection molded from plastic so as to have a plurality of dipwells 22—22 arrayed in patterns which correspond to the patterns in which the distal points 12 of the applicator 5 are arrayed or arranged. Preferably, upwardly extending the interior of each dipwell is generally semi-cylindrical at one upwardly extending end or side as indicated at 23 in FIG. 4 while the opposite end or side 24 is inclined and generally semi-conical. This configuration permits each dipwell 22 to have a maximum capacity or volume for a skin testing substance toward the top with a minimized capacity at the bottom whereat only a residual amount of a skin testing substance is desired. With this configuration, the capacity of each dipwell 22 can be most efficiently and readily utilized through a relatively shallow well. The shallow well enables the use of an applicator with relatively short U-shaped limbs 7—7. Long U-shaped limbs would create difficulties in use of the applicator.

The combined length of each leg 10 and its points 12 is such as to be slightly less than the depth of each dipwell 22. This relationship allows the points to be lowered into the dipwells until the horizontal bight sections 8 engage the top surface of the tray 20. Thus, the contents of each dipwell 22 can be substantially entirely utilized. Since the size or diameter of the legs 10 do not exceed or appreciably exceed, the diameters of the pointed ends 12 the ends can be lowered straight down to the bottom of each well without interference with the sidewalls of the wells 22.

It will be noted from FIGS. 1 and 3 that the multiple point distal ends 12—12 of the applicator 5 are arrayed in parallel rows of four each on opposite sides of the handle 6 in a symmetrical pattern. Likewise, the dipwells 22—22 in the tray 20 are arrayed in parallel rows of four each in patterns corresponding to the pattern in which the distal ends 12 are arranged. In use, assuming that the wells 22 are filled with skin testing substances, the objective is to simultaneously dip the distal ends 12 of an applicator 5 into each well 22 to substantially the same depth so that the points on the distal ends will pick up a load or dose of the desired medicament from each dipwell. It will be understood that the volume or amount of each dose or increment of medicament picked up is relatively small compared with the volume of the skin testing substance or medicament which each of the wells 22 can hold.

In order to assist the operator or user in quickly and accurately guiding the pointed distal ends 12 simultaneously to substantially the same depth in each of the dipwells 22, each of the three patterns or sets of dipwells 22 in the tray 20 is provided with an upright orienting pin 25 at one end and at the opposite end with an upright concave guide 26. The orienting or guide formation 13 on the handle 6 of the applicator 5 is co-operable with one of the guide or orienting posts 25 while the opposite post-like end 15 of the handle 6 is co-operable with a corresponding concave post-like guide formation 26.

Figure 4:
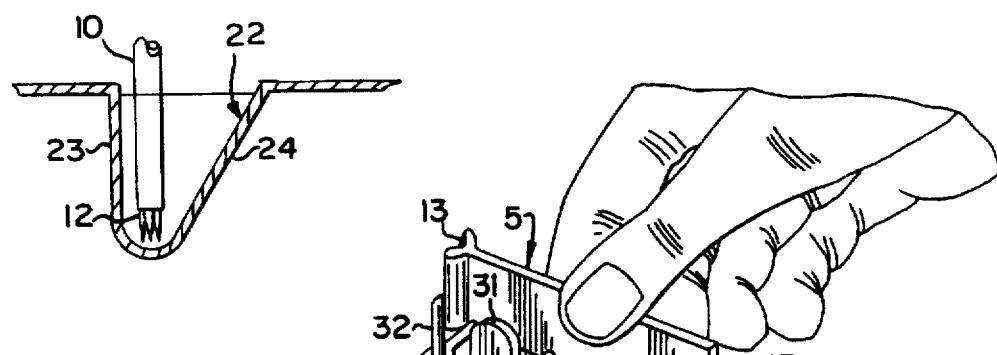
FIG. 4 is a fragmentary sectional view on enlarged scale taken on line 4—4 of FIG. 3.

From FIGS. 3 and 4 it will be seen that the orienting posts 25 and orienting guides 26 are so spaced and positioned that the guide formations 13 and 15 on the handle 6 are in mating cooperation therewith and each vertical leg 10 will be oriented so that its distal end 12 will be directly over the bottom of a dipwell 22 as shown in FIG. 4.

Since the top openings for the dipwells 22 are relatively large, the operator or user who is manipulating the adaptor 5 can readily observe the depths to which the pointed distal ends 12 should be lowered into the dipwell 22 in order to be immersed in the contents thereof sufficiently to pick up the desired doses or loads of skin testing substance.

Figure 5:
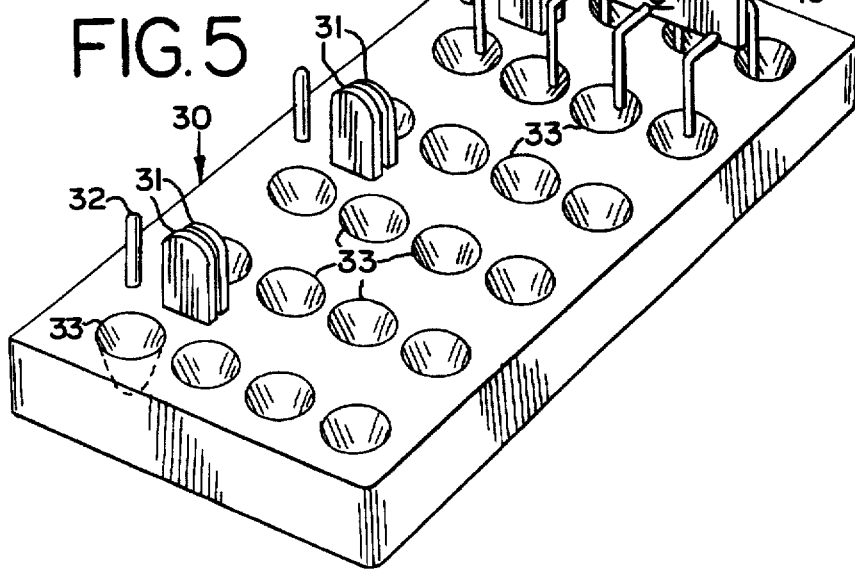
FIG. 5 is a perspective view of another embodiment of the invention illustrating how the applicator of FIGS. 1 and 3 is utilized with a correspondingly modified dipwell tray.

Referring to FIG. 5, the applicator 5 of FIGS. 1 and 3 is shown in use with a modified dipwell tray indicated generally at 30. The tray 30 corresponds to dipwell tray 20 of FIGS. 2, 3 and 4 except for one modification, namely, each concave guide 26 has been eliminated and replaced with a pair of upright parallel tabs 31—31. Upright orienting pins 32 have been retained corresponding to pins 25, and dipwells 33—33 have been retained corresponding to dipwells 22. The tabs 31 in each pair are spaced so as to readily receive the handle 6 of an applicator 5 therebetween with the distal ends 12 on the limbs 7 aligning with the bottoms of the dipwells 33. Each pair of tabs 31 is so located that when the guide formation 13 on an applicator 5 engages an orienting pin 32 the vertical edges of the tabs nearest the pin 32 will be engaged by the horizontal portions of the limbs 7 nearest the pin 32. Thus, each pin 32, each guide formation 13, each pair of limbs 7 juxtaposed to the formation 13 and each pair of tabs 31 jointly cooperate to readily guide and orient each applicator 5 with respect to a set of dipwells 33.

It will be understood by those skilled in the art that certain changes may be made in the embodiments of the invention shown and described and other embodiments of the invention may be provided without departing from the spirit and scope of the invention as defined in the appended claims.

What is claimed is:

1. In a multi-site skin testing applicator for simultaneously picking up multiple doses of skin test substances and making multiple skin tests therewith on spaced sites on a person's skin, said applicator comprising an elongated handle and a plurality of limbs extending outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle, the improvement comprising, at least one applicator orienting formation on said handle co-operable with an orienting formation on a dipwell tray having multiple dipwells for holding skin test substances therein with said dipwells being arrayed in at least one pattern which matches the pattern in which said co-planar distal ends are arrayed and having a dipwell orienting formation thereon co-operable with each said applicator orienting formation whereby said handle may be used to orient said arrayed distal ends in only one way with said arrayed dipwells and simultaneously dip said distal ends into said pattern of arrayed dipwells and thereafter withdraw said distal ends from said dipwells with skin test substances adhering to said dipped distal ends.

2. In the applicator called for in claim 1, wherein the cross-sectional size of the downwardly extending portions of said limbs is not appreciably greater than the cross-sectional size of said distal ends whereby said limbs will fit openings which said distal ends will fit into.

3. In the applicator called for in claim 1, wherein said handle of said applicator has a said applicator orienting formation on each end.

4. In the applicator called for in claim 3, wherein said orienting formations on said ends of said handle are different.

5. In the applicator called for in claim 1, wherein said limbs are arranged in pairs which extend transversely from opposite sides of said handle and one of said pairs serves as a second applicator orienting formation in cooperation with a second dipwell orienting formation on said dipwell tray.

6. In the applicator called for in claim 1, wherein said applicator orienting formation on the end of said applicator handle extends transversely to the length of said handle and has a vertically extending surface thereon which mates with a surface on a said dipwell orienting formation.

7. In the applicator called for in claim 1, wherein the applicator orienting formation on the opposite end of said handle is generally in the shape of a vertical post.

8. In a dipwell tray for use with a multi-site skin testing applicator and holding relatively large volumes of skin test substances in its dipwells to be withdrawn therefrom in relatively small increments and having at least one group of dipwells arrayed in a pattern which matches the pattern in which generally co-planar skin test substance pick-up distal ends are arrayed on said applicator for use in simultaneously making multiple skin tests on spaced sites on a person's skin whereby said applicator may be used to dip its said distal ends into each said group of dipwells and withdraw said dipped distal ends from said dipwells with small increments of skin test substances adhering to said withdrawn distal ends, the improvement comprising at least one dipwell orienting formation on said dipwell tray co-operable with an applicator orienting formation on said applicator whereby said distal ends on said applicator may be oriented in only one way with and simultaneously dipped into said group of dipwells.

9. In the dipwell tray called for in claim 8, wherein said dipwell orienting formation is in the form of a post.

10. In the dipwell tray called for in claim 8, wherein there are two said dipwell orienting formations upstanding on said dipwell tray one of which mates with an applicator orienting formation on one end of said applicator and the second of which mates with an applicator orienting formation on the opposite end of said applicator.

11. In the dipwell tray called for in claim 8, wherein each dipwell tapers downwardly from a wide top opening at least several times larger than a said skin test substance pick-up distal end to a narrow restricted bottom big enough to accommodate a said distal end.

12. In combination, an applicator for simultaneously making multiple skin tests on spaced sites on a person's skin comprising an elongated handle and a plurality of limbs extending outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle, and a dipwell tray for holding relatively large volumes of skin test substances in its dipwells to be withdrawn therefrom by said distal ends on said applicator limbs in relatively small increments and having at least one group of dipwells arrayed in a pattern which matches said pattern in which said distal ends are arrayed, the improvements comprising at least one set of co-operable interengaging orienting formations on said applicator and dipwell tray which cooperate to orient said distal ends on said applicator with each said group of dipwells in only one way so as to facilitate the simultaneous dipping of said distal ends into the skin test substances in each said group of dipwells.

13. In the combination called for in claim 12, wherein said at least one set of co-operable interengaging orienting formations comprises a transversely extending formation on one end of said applicator handle and an upstanding post on said dipwell tray.

14. In the combination called for in claim 12, wherein there are two said sets of co-operable orienting formations which are positioned to orient opposite ends of said applicator with opposite ends of each said group of dipwells.

15. In the combination called for in claim 12, wherein each said set of orienting formations includes one formation having an interengaging surface which mates with a mating interengaging surface on the other formation.

16. In the combination called for in claim 14, wherein one of said two sets comprises a transversely extending formation on one end of said applicator handle and an upstanding post on said dipwell tray.

17. In the combination called for in claim 16, wherein the other of said two sets comprises an intermediate portion of said applicator handle and a pair of upstanding spaced parallel tabs positioned to receive therebetween said intermediate portion of said applicator handle.

18. In the combination called for in claim 17, wherein said limbs on said applicator handle are arranged in pairs which extend transversely from opposite sides of said applicator handle and one of said pairs serves as an applicator orienting formation in cooperation with said pair of said upstanding spaced parallel tabs.

19. In combination, an applicator for simultaneously making multiple skin tests on spaced sites on a person's skin comprising an elongated handle and a plurality of limbs extending outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle, and a dipwell tray for holding relatively large volumes of skin test substances in its dipwells to be withdrawn therefrom by said distal ends on said applicator limbs in relatively small increments and having at least one group of dipwells arrayed in a pattern which matches said pattern in which said distal ends are arrayed, the improvements which comprise each said dipwell having a relatively large top opening and a bottom of relatively small area and each said limb on said handle being generally U-shaped with the bight portion thereof being in the form of arms extending outwardly from opposite sides of said handle and with the legs thereof extending generally vertically downwardly from the outer ends of said arms, the combined length of each said leg and its said distal end being slightly shorter than the depths of said dipwells whereby when said distal ends are lowered into said dipwells to the maximum extent, portions of said applicator will engage said dipwell preventing further lowering of said distal ends which will be spaced slightly above said small area bottoms of said dipwells.

20. The combination called for in claim 19, wherein said top openings of said dipwells are generally co-planar with the top surface of said dipwell tray and said bight portions of said U-shaped limbs engage said top surface and thereby limit said maximum extent to which said distal ends can be lowered into said dipwells.

21. The combination called for in claim 19 wherein said applicator and said dipwell tray have cooperating orienting formations thereon which orient said distal ends directly over said dipwell bottoms.

22. In a multi-site skin testing applicator for simultaneously picking up multiple doses of skin test substances and making multiple skin tests therewith on spaced sites on a person's skin, said applicator comprising an elongated handle and a plurality of limbs extending outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle the improvement comprising, at least one applicator orienting formation on said handle co-operable with an orienting formation on a dipwell tray having multiple dipwells for holding skin test substances therein with said dipwells being arrayed in at least one pattern which matches the pattern in which said co-planar distal ends are arrayed and having a dipwell orienting formation thereon co-operable with each said applicator orienting formation whereby said handle may be used to orient said arrayed distal ends with said arrayed dipwells and simultaneously dip said distal ends into said pattern of arrayed dipwells and thereafter withdraw said distal ends from said dipwells with skin test substances adhering to said dipped distal ends and, wherein said handle of said applicator has a said applicator orienting formation at each end, and said applicator orienting formations are different from each other and one formation extends transversely to the length of said handle and has a vertically extending concave surface which mates with a convex surface on a said dipwell orienting formation.

23. In a dipwell tray for use with a multi-site skin testing applicator and holding relatively large volumes of skin test substances in its dipwells to be withdrawn therefrom in relatively small increments and having at least one group of dipwells arrayed in a pattern which matches the pattern in which generally co-planar skin test substance pick-up distal ends are arrayed on said applicator for use in simultaneously making multiple skin tests on spaced sites on a person's skin whereby said applicator may be used to dip its said distal ends into each said group of dipwells and withdraw said dipped distal ends from said dipwells with small increments of skin test substances adhering to said withdrawn distal ends the improvement comprising at least one dipwell orienting formation on said dipwell tray co-operable with an applicator orienting formation on said applicator whereby said distal ends on said applicator may be oriented with and simultaneously dipped into said group of dipwells and wherein there are two said dipwell orienting formations upstanding on said dipwell tray one of which mates with an applicator orienting formation on one end of said applicator and the second of which mates with an applicator orienting formation on the opposite end of said applicator, and one of said upstanding dipwell orienting formations is a post with a convex surface and the other is a generally rectangular post with a concave surface.

24. In a dipwell tray for use with a multi-site skin testing applicator and holding relatively large volumes of skin test substances in its dipwells to be withdrawn therefrom in relatively small increments and having at least one group of dipwells arrayed in a pattern which matches the pattern in which generally co-planar skin test substance pick-up distal ends are arrayed on said applicator for use in simultaneously making multiple skin tests on spaced sites on a person's skin whereby said applicator may be used to dip its said distal ends into each said group of dipwells and withdraw said dipped distal ends from said dipwells with small increments of skin test substances adhering to said withdrawn distal ends the improvement comprising at least one dipwell orienting formation on said dipwell tray co-operable with an applicator orienting formation on said applicator whereby said distal ends on said applicator may be oriented with and simultaneously dipped into said group of dipwells and wherein there are two said dipwell orienting formations upstanding on said dipwell tray one of which mates with an applicator orienting formation on one end of said applicator and the second of which mates with an applicator orienting formation on the opposite end of said applicator, and one of said upstanding dipwell orienting formations is a post and the other is a pair of parellel tabs spaced and oriented to receive therebetween the handle of a said applicator.

25. In a dipwell tray for use with a multi-site skin testing applicator and holding relatively large volumes of skin test substances in its dipwells to be withdrawn therefrom in relatively small increments and having at least one group of dipwells arrayed in a pattern which matches the pattern in which generally co-planar skin test substance pick-up distal ends are arrayed on said applicator for use in simultaneously making multiple skin tests on spaced sites on a person's skin whereby said applicator may be used to dip its said distal ends into each said group of dipwells and withdraw said dipped distal ends from said dipwells with small increments of skin test substances adhering to said withdrawn distal ends the improvement comprising at least one dipwell orienting formation on said dipwell tray co-operable with an applicator orienting formation on said applicator whereby said distal ends on said applicator may be oriented with and simultaneously dipped into said group of dipwells and wherein there are two said dipwell orienting formations upstanding on said dipwell tray one of which mates with an applicator orienting formation on one end of said applicator and the second of which mates with an applicator orienting formation on the opposite end of said applicator, and one wall of each dipwell is generally semi-cylindrical and the opposing wall is generally semi-conical.

26. In combination, an applicator for simultaneously making multiple skin tests on spaced sites on a person's skin comprising an elongated handle and a plurality of limbs extending outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle, and a dipwell tray for holding relatively large volumes of skin test substances in its dipwells to be withdrawn therefrom by said distal ends on said applicator limbs in relatively small increments and having at least one group of dipwells arrayed in a pattern which matches said pattern in which said distal ends are arrayed the improvements comprising at least one set of co-operable interengaging orienting formations on said applicator and dipwell tray which cooperate to orient said distal ends on said applicator with each said group of dipwells so as to facilitate the simultaneous dipping of said distal ends into the skin test substances in each said group of dipwells, and wherein there are two said sets of co-operable orienting formations which are positioned to orient opposite ends of said applicator with opposite ends of each said group of dipwells, one of said two sets comprises a transversely extending formation on one end of said applicator handle and an upstanding post on said dipwell tray and wherein the other of said two sets comprises and post formation with a convex surface on the opposite end of said applicator handle and an upstanding generally rectangular post with a concave surface on said dipwell tray.

* * * * *